(12) United States Patent
Lavi et al.

(10) Patent No.: US 10,610,251 B2
(45) Date of Patent: Apr. 7, 2020

(54) MEDICAL DEVICE FOR TISSUE REMOVAL

(71) Applicants: Sanoculis Ltd., Kiryat Ono (IL); TEL HASHOMER MEDICAL RESEARCH INFRASTRUCTURE AND SERVICES LTD., Ramat Gan (IL)

(72) Inventors: Gilad Lavi, Rishon Le'zion (IL); Yoseph Glovinsky, Petah Tiqwa (IL); Vadim Shmukler, Rishon Le'Zion (IL); Nir Israeli, Kiryat Ono (IL)

(73) Assignees: SANOCULIS LTD., Kiryat Ono (IL); TEL HASHOMER MEDICAL RESEARCH INFRASTRUCTURE AND SERVICES LTD., Ramat Gan (IL)

(*) Notice: Subject to any disclaimer, the term of this patent is extended or adjusted under 35 U.S.C. 154(b) by 412 days.

(21) Appl. No.: 15/129,164

(22) PCT Filed: Mar. 26, 2015

(86) PCT No.: PCT/IL2015/050324
§ 371 (c)(1),
(2) Date: Sep. 26, 2016

(87) PCT Pub. No.: WO2015/145444
PCT Pub. Date: Oct. 1, 2015

(65) Prior Publication Data
US 2017/0112520 A1 Apr. 27, 2017

(30) Foreign Application Priority Data
Mar. 27, 2014 (IL) .......................................... 231751

(51) Int. Cl.
*A61B 17/32* (2006.01)
*A61B 10/02* (2006.01)
*A61F 9/007* (2006.01)
*A61B 17/16* (2006.01)
*A61B 17/34* (2006.01)
*A61B 90/00* (2016.01)

(52) U.S. Cl.
CPC .... *A61B 17/32002* (2013.01); *A61B 10/0266* (2013.01); *A61B 17/1615* (2013.01);
(Continued)

(58) Field of Classification Search
CPC ................................................. A61B 17/32002
See application file for complete search history.

(56) References Cited

U.S. PATENT DOCUMENTS 5,263,974 A * 11/1993 Matsutani .............. A61B 17/00
606/222
6,837,896 B2 1/2005 Matsutani et al.
(Continued)

FOREIGN PATENT DOCUMENTS

CN 1387829 A 1/2003
CN 1882282 A 12/2006
(Continued)

*Primary Examiner* — Richard G Louis
(74) *Attorney, Agent, or Firm* — Browdy and Neimark, P.L.L.C.

(57) ABSTRACT

The present disclosure provides medical devices for creating a channel in a biological soft tissue. The devices comprise an integral rotatable tool formed by an elongated distal member and a proximal shaft, the elongated member having a distal end portion and a proximal end portion, the distal end portion comprising a tissue piercing tip of a pyramid-like shape, and the proximal end portion comprising an elongated prism-like portion having at least three surfaces and respective prism edges, with at least one of the prism edges between the surfaces being configured as a tissue cutting blade, and the proximal shaft interfacing and extending from the prism-like portion and having a cross section larger than a cross section of the prism-like portion at the interface. In some embodiments, the device comprises an intermediate portion extending between the distal end portion and the proximal end portion and having a frustum shape, thereby (Continued)

forming a smooth transition between a base portion of the tissue piercing tip and the proximal end portion.

22 Claims, 8 Drawing Sheets

(52) U.S. Cl.
CPC ...... *A61B 17/1633* (2013.01); *A61F 9/00709* (2013.01); *A61F 9/00736* (2013.01); *A61B 17/3476* (2013.01); *A61B 2017/320056* (2013.01); *A61B 2017/3454* (2013.01); *A61B 2090/034* (2016.02); *A61B 2090/036* (2016.02); *A61F 9/00781* (2013.01)

(56) References Cited

U.S. PATENT DOCUMENTS

| | | |
|---|---|---|
| 2003/0004527 A1 | 1/2003 | Matsutani et al. |
| 2004/0006358 A1 | 1/2004 | Wulfman et al. |
| 2004/0106948 A1 | 3/2004 | Cunningham |
| 2005/0149088 A1 | 7/2005 | Fukuda et al. |
| 2005/0245950 A1* | 11/2005 | Kozlowski ......... A61B 17/3211 606/167 |
| 2006/0100654 A1* | 5/2006 | Fukuda ............ A61B 5/150022 606/181 |
| 2009/0112119 A1 | 4/2009 | Kim |
| 2010/0146799 A1* | 6/2010 | Hoffman ............ A61B 17/3211 30/286 |

FOREIGN PATENT DOCUMENTS

| | | | | |
|---|---|---|---|---|
| DE | 10223253 A1 | 11/2002 | | |
| EP | 1695664 A1 | 12/2004 | | |
| EP | 1875873 A1 | 6/2007 | | |
| EP | 2039300 A1 | 7/2007 | | |
| EP | 1875873 A1 * | 1/2008 | ......... | A61B 17/3211 |
| JP | 2005-177302 | 7/2005 | | |
| RU | 2054895 C1 | 2/1996 | | |
| WO | 2013186779 A2 | 12/2013 | | |

\* cited by examiner

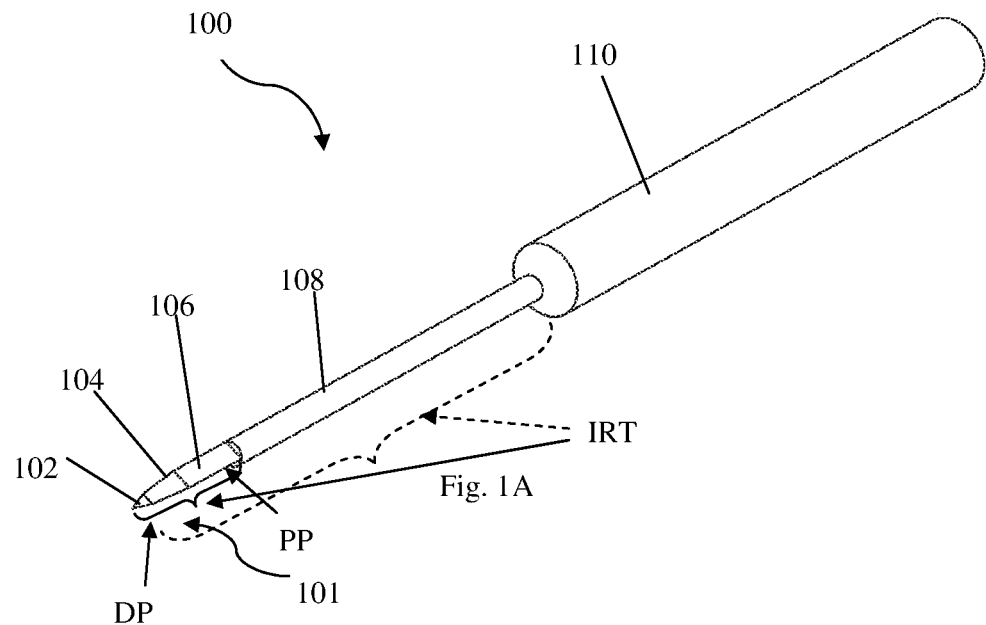
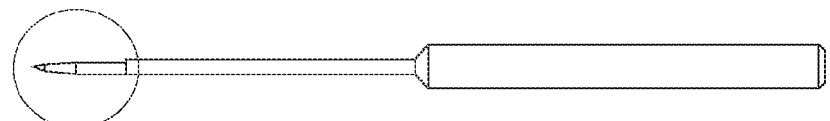
Fig. 1B
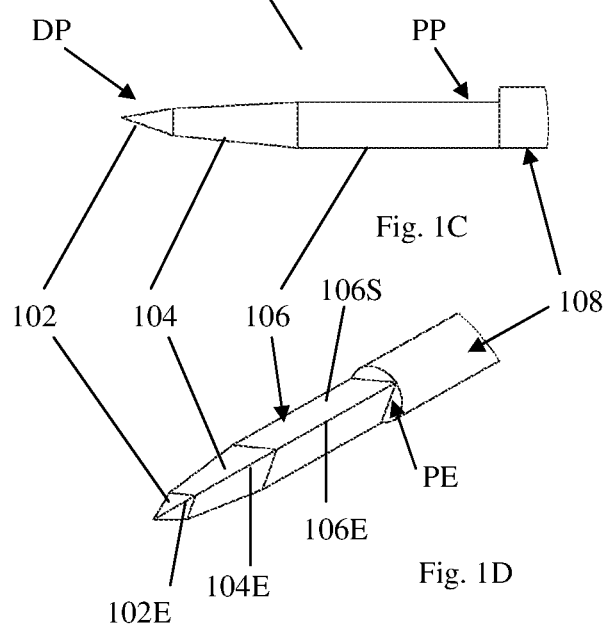

US 10,610,251 B2

MEDICAL DEVICE FOR TISSUE REMOVAL

TECHNOLOGICAL FIELD

The present disclosure relates to surgical tools.

BACKGROUND

In medical procedures, a need frequently arises to cut and remove small volumes of tissue from the body as a treatment or for diagnosis purposes. This may be essential, for example, during acquiring tissue for a biopsy, removing calcification from inner walls of obstructed blood vessels or creating paths for drainage of excessive liquids such as in Glaucoma condition. Tools are available for cutting soft as well as hard tissues in the body.

In WO 2013/186779, to the assignee of the present application the content of which incorporated herein by reference, a medical device, an assembly comprising the device and a method making use of same are disclosed. The device comprises an elongated member extending between a first end and a second end, and a segment proximal to the second end extending along a longitudinal axis X, said segment comprising at least one depression axially extending along at least a portion of said segment and an external surface having a circumference C; and one or more blades with a cutting edge peripheral to C and the one or more blades extending along at least part of said segment; the first end comprising an engagement element for engagement with a grip unit comprising a rotor to cause rotation of said device about said axis upon actuation of the rotor and the second end comprising a tissue piercing tip.

GENERAL DESCRIPTION

The present disclosure provides a novel medical device for creating a channel in a biological soft tissue. For example, this may be a channel in the sclero-corneal junction of a subject's eye, which may be used when drainage of fluid is required as a treatment of a medical condition. In some embodiments, the channel may be useful for reducing intraocular pressure by providing fluid communicating between the anterior chamber of the eye and the interface between the sclera and the conjunctiva.

The medical device of the present invention is configured to optimize the device penetration to the tissue followed by tissue cutting to form a channel, while eliminating a need of cutting elements projecting from the device body. In this connection, it should be understood that the medical device of the invention is configured and operable to provide smooth penetration to the tissue under minimal penetration force being applied on the device and accordingly on the tissue, i.e. with minimized threshold force thereby saving over shoot required to overcome it.

Further, the medical device of the present invention is configured to cut tissue and form the channel upon rotation, while mere insertion of the device into a tissue, when not involving rotation, does not cause significant damage in the tissue. Therefore, generally, the medical device is configured to operate in three distinct phases, an insertion phase characterized by an essentially linear movement of the device along its linear longitudinal axis into the target tissue, a rotation phase during which an integral rotatable tool of the device is rotated around its linear longitudinal rotation axis and a withdrawal phase in which the device is removed from the tissue. The withdrawal phase may be with or without rotation depending, inter alia, on the tissue characteristics (kind, stiffness, region in the body), the time of operation and the desired channel shape.

Thus, according to a broadest aspect of the invention, there is provided a medical device for creating a channel in a biological soft tissue, the device comprising an integral rotatable tool formed by an elongated distal member and a proximal shaft, the elongated member having a distal end portion and a proximal end portion, said distal end portion comprising a tissue piercing tip of a pyramid-like shape, and said proximal end portion comprising an elongated prism-like portion having at least three surfaces and respective prism edges, with at least one of the prism edges between the surfaces being configured as a tissue cutting blade, and said proximal shaft interfacing and extending from said prism-like portion and having a cross section larger than a cross section of the prism-like portion at the interface.

It should be noted that for the purposes of the present disclosure, the pyramid-shaped piercing tip may have straight or rounded edges between the surfaces of the pyramid, as well as may have planar or curved surfaces, and therefore the term "pyramid" as used herein should be interpreted broadly. Also, the elongated prism-like portion may be of any polygonal cross-sectional geometry, and may thus include more than three surfaces/sides. Generally, not all the edges between the surfaces may be configured as tissue cutting blades, and thus, generally, that/those edge(s) which are not intended to cut the tissue may or may not be rounded. Preferably, however, all the edges of the prism-like portion are blades. Also, the surfaces of the prism-like portion may be planar or curved. Further, the prism-like portion may be of the same cross-section, or may have gradually increasing/decreasing cross-section, i.e. having a frustum geometry. Therefore, the term "prism" or "prism-like portion" should also be interpreted broadly for the purposes of the present disclosure. Further, it should be noted that the term "cutting" or "cut" as used herein refer to tissue removal by cutting or scraping.

Generally, a polygonal geometry may be defined by its circumscribed circle and inscribed circle. Accordingly, a prism defines circumscribed and inscribed surfaces. When such prism with at least one tissue cutting blade is being rotatable about its longitudinal axis it cuts a ring-like tissue portion having a thickness corresponding to the difference between the circumscribed circle and an inscribed circle of the prism. Accordingly, the medical device of the present invention is configured for operation while rotating said integral tool inside a tissue to be cut. The tool is straight and symmetrical along its longitudinal linear axis, and rotates symmetrically around its longitudinal linear axis. As such, the axis of rotation (i.e., the longitudinal linear axis) exists within the tool body.

The space between the circumscribed circle and the prism's surfaces defines a corresponding number of gaps, i.e. at least three gaps for the prism of at least three surfaces. These gaps (usually identical) actually form grooves for collecting tissue removed as a result of rotation of the prism.

According to another broad aspect of the invention, a medical device for creating a channel in a biological soft tissue is provided comprising an integral rotatable tool formed by an elongated distal member and a proximal shaft, the elongated distal member having a distal end portion comprising a tissue piercing tip of a pyramid-like shape, an intermediate portion, and an proximal end portion comprising one or more tissue cutting elements, the intermediate portion being extending between the distal end portion and the proximal end portion and having frustum shape thereby forming a smooth transition between a base portion of the tissue piercing tip and the proximal end portion.

In some embodiments of the invention, the above two configurations are combined, and thus the elongated member comprises three successive portions, a distal portion with a tissue piercing tip of a pyramid shape, an intermediate portion of frustum geometry extending from a base of the pyramid, and a proximal end portion comprising an elongated prism having at least three sides and respective prism edges with at least one of the prism edges between the sides being configured as a tissue cutting blade.

In some embodiments, the intermediate portion has a cross section of polygon geometry, corresponding to the base of the tissue piercing tip, with a cross sectional dimension increasing towards the proximal end portion (e.g. towards the elongated prism).

In some embodiments, the elongated member has a projection at the vicinity of the proximal portion that functions as a penetration stopper defining the maximal penetration depth of the device into the tissue.

In some embodiments, the elongated member, at its proximal end portion, is configured for attaching to a shaft. In some embodiments, the device at its proximal end portion comprises an engagement element for attachment with the shaft. In some other embodiments, the proximal end portion comprises a shaft integral with and extending from the proximal end portion (e.g. from the elongated prism); i.e. the medical device, which comprises the distal tissue-piercing end portion, the elongated prism-like portion and the shaft (and optionally the intermediate frustum-shape portion), is unibody made from one-piece. The shaft is, therefore, fixed with the medical device and rotates on its axis with it, when it is integral as well as when it is attached.

The transition from the polygonal cross-section (e.g. the prism) to the round shaft provides a stopping feature enabling to define the preferred axial position (full penetration). Preferably, the transition is sudden and sharp formed by a right angle at the border between the prism and the shaft. In other words, an interface between the elongated member and the shaft forms a stopper defining the maximal penetration depth of the device into the tissue. User can sense the arrival to the full penetration state due to the increase in forwarding force (minimization of penetration force decreases the effect of threshold and enables controlled insertion of the tool into the tissue). The transition between the shaft and the prism is also defined by its difference in cross section, as further described herein.

In some embodiments, the device further comprises a protective sleeve surrounding the shaft along at least a distal part thereof at the proximal end portion of the elongated member, and being configured to allow the shaft rotation inside and relative to the protective sleeve. The protective sleeve may be provided as an external part surrounding the device. In some embodiments, during operation of the device the protective sleeve is fixed in place with respect to the soft tissue, so as to at least provide protection of the soft tissue at a distal part of the proximal end portion of the elongated member.

The shaft by its free end may be connectable to an external shank, or alternatively, the device may comprise a shank with its one end being connectable to or integral with the shaft.

The device may be configured for connecting via its proximal end to a driving unit.

The device of the present invention has a simple configuration, is relatively easy to manufacture, and requires no sophisticated processes. At the same time, it is highly effective in cutting soft tissue. The device described in all embodiments herein is preferably manufactured from one piece, making the manufacturing process even easier and cost effective while giving the device robustness (due to polygonal cross-section of the cutting portion) and durability.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIGS. 1A to 1H illustrate an example of a medical device according an embodiment of the invention; where FIG. 1A is a schematic isometric view of the device, FIG. 1B is a side view of the device of FIG. 1A, FIGS. 1C and 1D are zoomed views of a part of the device involved in the tissue cutting procedure, and FIGS. 1E to 1H exemplify dimensions (relative) and shapes for the different parts of the device;

DETAILED DESCRIPTION OF EMBODIMENTS

Figure 1E:
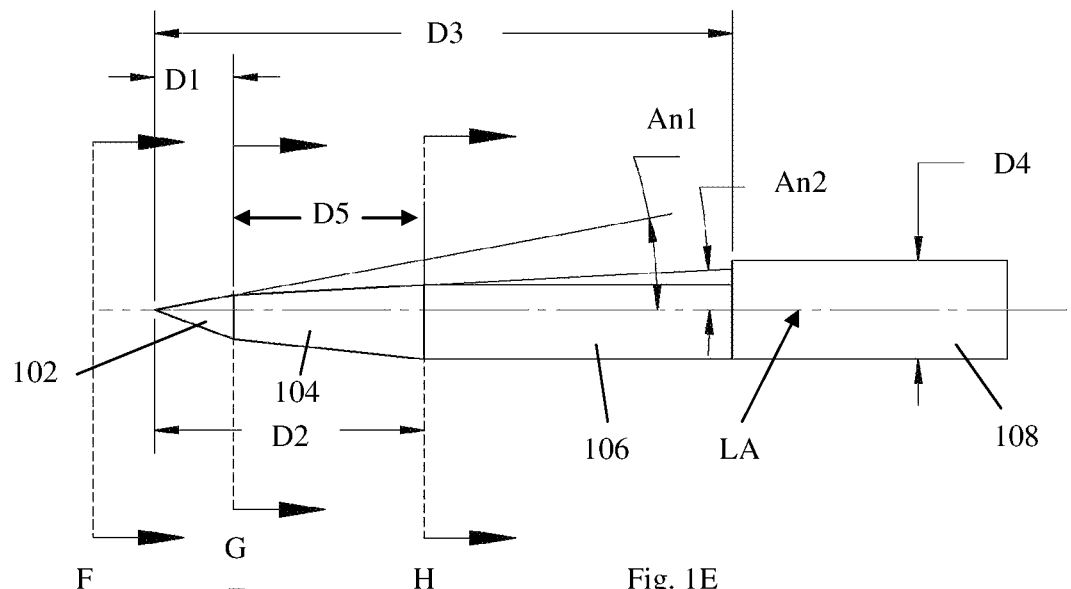

The present disclosure is directed to a medical device configured and operable to cut soft tissue in a well-defined manner including, but not limited to, the shape and volume of the excised tissue, in relatively short duration of the cutting procedure, with minimum invasion and consequently minimum discomfort to the treated subject. As a non-limiting example, the device may be used in treating Glaucoma and high intraocular pressure, such that a channel is created in the sclera tissue of the eye, so that the excess of fluid inside the eye, causing the Glaucoma, escapes the eye through the created channel and relieves the anterior chamber of the eye.

Reference is made to FIGS. 1A to 1H showing a specific but non limiting example of a medical device 100 according to some embodiments of the present invention. The device 100 includes an integral rotatable tool IRT including an elongated member 101 having distal and proximal end portions, DP and PE, respectively. The distal end portion DP includes a tissue piercing tip 102 of a pyramid-like geometry/shape, and the proximal end portion PP is configured as a cutting tool and includes at least one cutting element. In the present example, the proximal end portion PP includes an elongated prism-like portion/member 106 having at least three surfaces/sides (planar or curved) 106S, with at least one of prism edges 106E between the sides being configured as a tissue cutting blade. Sometimes, some of these parts of the device will be referred to herein after as a piercing section for the piercing tip 102 and a cutting section for the elongated prism 106.

Optionally, the device may also include some or all of the following parts shown in the figures: an intermediate, penetrating section/portion 104, a shaft 108, and a shank 110. The role of all these optional parts will be described below.

The device 100 is configured to pierce a soft tissue being treated from the distal end portion DP of the device through the piercing tip 102, be progressed through (penetrate) the tissue and after being positioned inside the tissue at a desired location, i.e. such that the tissue to be cut is surrounded by the elongated cutting prism 106, the device is operated for rotation with appropriate speed, and the surrounded tissue is thus cut/scraped by the cutting blade(s) provided along the prism edge(s) 106E. Eventually and after a predetermined number of revolutions or a predetermined time of rotation, a channel is created in the treated tissue. The number of rotations, speed of rotation and time of rotation may control the final resulting channel, when more of each means wider channel, until reaching the maximum channel width dictated by the geometrical dimensions of the device. With the device configuration of the invention, the given channel is formed by relatively low number of turns/revolutions and the channel dimension is maintained even if the cutting tool goes on rotating. This feature is important because it minimizes the risk of side move (surgeon losing control) that will cause for bigger channel than required. It should be understood, that this feature is obtained because the device has a straight longitudinal axis around which it rotates symmetrically.

The piercing tip 102, as said above, has a form of a pyramid, with a polygonal base. The polygon is usually equilateral, e.g. an equilateral triangle, a square (quadrilateral), a hexagon, etc. Preferably, and as shown in the current non-limiting example (FIG. 1F), the pyramid has a triangular base. The inventors have found that the triangular pyramid is more effective in piercing and is effectively more tolerated by the pierced tissue causing minimum discomfort to the treated subject.

The cutting section 106 has a form of elongated prism, i.e. its cross-section (transverse diameter) is small relative to its longitudinal dimension. The prism 106 has a polygonal base, preferably an equilateral polygon, such as an equilateral triangle, a square, a hexagon and the like. In some embodiments, the piercing tip 102 and the elongated prism 106 form a one continuous shape, in this case, both have the same polygon base having the same number of sides/surfaces and the same cross-sectional area. In some other embodiments, the bases of the piercing and cutting sections may be different; they might be polygons of different number of sides or polygons of different cross sectional areas, or different in both aspects. In the example shown in FIGS. 1A-1F, the bases of the pyramid and prism have the same number of sides but different areas.

As already described, the prism 106 has at least one of its edges at the borders between the surfaces/sides being configured as a cutting blade. Usually, a prism inherently has a cutting property at its edges, if the prism is crafted with precision and made from hard metals. In some other case, the edge/s is/are specially sharpened to provide the cutting blade/s.

As shown in the example of FIGS. 1A-1F, the elongated member 101 may also include an intermediate portion 104 positioned between the piercing and cutting parts, i.e. extending between the base of the pyramid-shaped tip and the cutting section, which preferably comprises the above-described elongated prism with at least one edge configured as a tissue cutting blade. The intermediate part 104 serves as a penetrating section of the elongated member 101, and has a frustum geometry configured as a smooth transition between the base portion of the tissue piercing tip 102 and the elongated prism 106. As described above, this minimizes the penetration force/threshold and maximizes robustness.

In the example of device 100, the penetrating section 106 has two triangular bases being identical to the base of the piercing section at one side and to the base of the cutting section (prism) at the other side. The edges of the frustum 104E are smoothly continuous with the edges of both the piercing tip 102E and the prism 106E, so that the penetration of the device into the soft tissue is done with relatively low force. The device configuration is aimed at reducing the penetration force since it is planned to avoid any peripheral tensioning of the tissue, to cut the tissue while penetrating it. Additionally and as will be described below, the inclination (slope) of the penetrating section is usually smaller than that of the piercing section, thus lowering the required force to be applied after the piercing is done.

As indicated above, the device preferably includes a stopper defining the maximal depth of the device penetration into the tissue. Such a stopper may be implemented as a rim-like projection at a certain location on a circumference of the proximal portion of the elongated member. Such a stopper projection PE is exemplified in FIG. 1D. In this example, however, the device is shown as including a shaft 108 that is integral or attached to a proximal end of the proximal portion of the elongated member 101. The shaft may have a larger cross section, thus forming a stopper PE for the device penetration into the tissue at the interface between the elongated member and the shaft. The transition between the prism and the shaft is sharp and immediate, formed by a right angle at the interface, thus a depression is formed from the point at the interface between the shaft and the cutting prism, such that the shaft's cross-section is larger than the cross section of all the different sections of the device towards its distal side (towards the piercing section). For example, the shaft's diameter may correspond to that of circumscribed circle of the prism. It should, however, be understood that a stopper feature may be part of the proximal portion of the elongated member and be independent of the shaft.

The shaft 108 is usually of elongated cylindrical shape (circular/rounded cross section) though it may have some other shapes such as a prism (polygonal cross section). The shaft 108, if used, provides for one or more of the following: it lengthens the device so that it can be mounted comfortably at a driving unit, e.g. a rotating machine, and/or enables reaching deeper tissues; it increases the mechanical strength of the device, giving it more rigidity and volume, especially during rotation. It should be noted that the interface between the cutting section and the shaft may be configured to form a stopper that limits the extra insertion of the device into the tissue and helps an operator to control the extent of penetration/insertion so that the device would be positioned accurately inside the tissue and the intended use of the device (cutting the tissue) is performed effectively. The stopping function of the shaft also eliminates or at least significantly reduces the need to apply axial force on the device during rotation. In case the shaft plays the role of a stopper, its cross sectional dimension is larger than the cross sectional dimension of the cutting part 106. This is shown clearly in FIGS. 1C and 1D. On the other side, while the shaft's cross sectional dimension is larger than that of the cutting prism 106, it is still small enough to enable insertion of the device into some tissues in the way until arriving at the tissue to be cut. For example, in order to get the device into the sclera of the eye, the device including the shaft passes through the conjunctiva.

It should be noted, and will be described more specifically further below, that in some embodiments, the integral rotatable tool IRT is formed by the above-described elongated member 101 (with or without the intermediate portion 104) and the shaft 108. In this case, the tool has a unibody or one-piece configuration.

Whether integral (unibody) or attached to the proximal end portion of the cutting prism, the shaft 108 is fixed firmly along the straight longitudinal axis of the device and rotates with the device during action.

A shank 110 may be also provided, being attached to the proximal side of the shaft 108. The shank 110 functions as an extension part of the device, so it can comfortably be mounted on a driving unit (rotating machine), and as a strengthening part to the device, that sometimes might be needed for high speed rotation of the cutting section during the treatment. As the shank 110 is not aimed at penetrating any tissue and staying always outside the body, its cross sectional dimension can be as large as desired, as required in a specific application. Similarly to the shaft, the shank may have a circular or polygonal cross section.

Referring to FIGS. 1E to 1H, several characteristic dimensions and cross sectional views of the device 100, are exemplified.

In FIG. 1E, a side view of the device 100 is shown. As can be seen, the piercing tip 102 has a total length D1 and a slope angle An1, being an angle of its outer surface relative to the longitudinal axis LA of the elongated member 101. The penetrating, intermediate section 104 has a length D5=(D2−D1) and a slope angle An2 relative to the longitudinal axis. The cutting section has a length (D3−D2) and zero slope. The shaft 108 has a cross sectional dimension (diameter) D4.

Figure 1F:
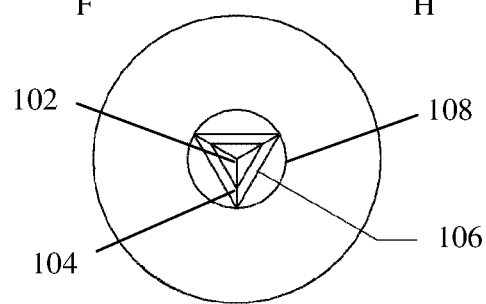
Figure 1G:
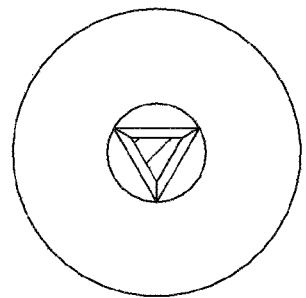
Figure 1H:
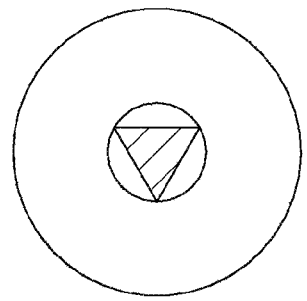

FIGS. 1F to 1H are the cross section views of the elongated member 101 together with its associated shaft and shank, taken along the lines F, G and H respectively.

The slope angle An2 of the penetrating section 104 is usually equal to or smaller than the slope angle An1 of the piercing section 102. The penetrating section adds robustness to the device, while at the same time helps in providing smooth continuous penetration under reduced applied force than one that would be required if the piercing tip (having a larger slope angle) extends along the whole dimension D2, while the piercing section cannot be of too small slope as in this case it will have to be longer and thus of less mechanical strength. Thus, due to the smoothness provided by the smaller slope of the penetrating section as compared to that of the piercing section, the piercing and penetration modes are more effective. The device penetrates under minimal force and minimizes the threshold force to save over shoot following overcoming it. The two slope angles of the piercing and penetrating sections define the transition point between these sections, i.e. the values D1 and D5 are affected by the slope values An1 and An2, and vice versa.

It should be noted that the device can be constructed in various shapes, volumes and dimensions. The device 100, for example, is constructed from a triangular pyramid at the piercing section 102, a triangular frustum at the penetrating section 104 and a triangular prism at the cutting section 106. Further, the device includes the shaft 108 and shank 110 having cylindrical circular shapes.

The dimensions of each part of the device are determined in view of the specific application. As an example, the following dimensions may be used to construct a device adapted to create a channel in an eye of a subject for treating high intraocular pressure:

D1=0.3-0.6 mm; D2=1-2 mm; D3=2.5-4 mm; D4=0.3-0.6 mm; An1=10-12.5°; An2=1-3°.

Figure 2:
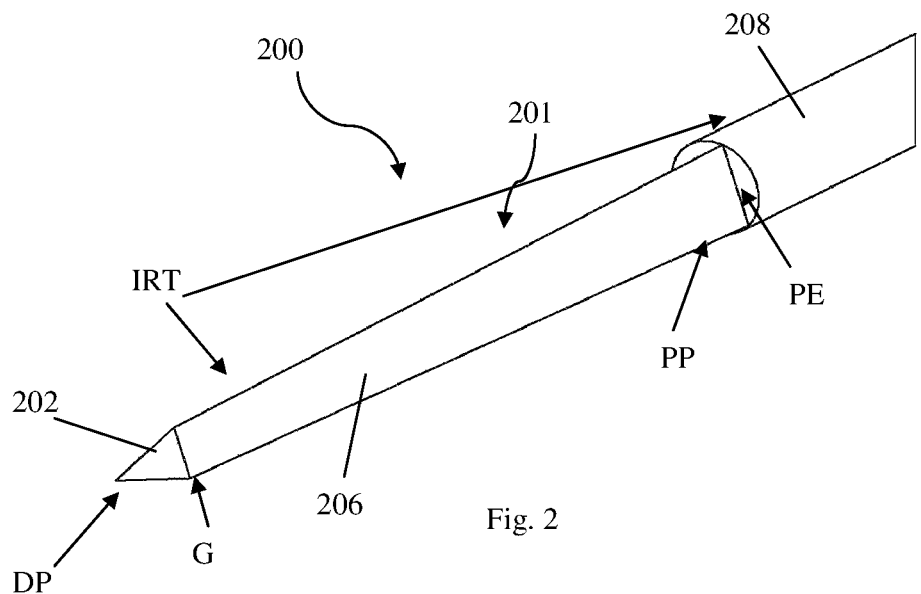
FIG. 2 shows an example of a medical device according to another embodiments of the invention, where the device does not include a penetrating smoothing portion, and the cutting section has a frustum geometry thus providing smoothness of penetration as well.

Reference is made to FIG. 2 showing another non limiting example of a device 200, according to some embodiments of the invention. To facilitate understanding in this illustrated figure and the following figures, the functional parts having the same function as in device 100 are assigned the same reference numbers with an addition of multiplications of 100. Thus, as shown in the figure, the device 200 includes an integral rotatable tool IRT formed by an elongated member 201 and a shaft 208. The elongated member has distal and proximal end portions, DP and EP, where distal end portion DP includes a tissue piercing tip 202, and the proximal end portion PP is configured as a cutting elongated prism-like member 206, i.e. prism with at least one edge configured as a cutting blade. The elongated member 201 at a proximal end of its proximal portion PP interfaces the shaft 208 (partly shown), which has a cross section larger than the cross section of the elongated member at the interface with the shaft. All these parts are configured as explained above in connection to device 100. Though a shank is not seen in the figure, it should be noted that it is always possible to include a shank in this configuration or in any other configuration of the device. The device 200 in this embodiment has the elongated member 201 which has no penetrating section (104 in FIGS. 1A-1H) between the piercing and cutting sections. Accordingly, the cutting section 206 has a direct interface G with the pyramid base of the piercing section 202. Also, in this example, the cutting prism-like section 206 has a frustum geometry, with the prism-base at the interface G matching the base of the pyramid of the piercing section 202 and the prism-base at an interface with a shaft being larger, or in other words the cross-section of the prism-like portion gradually increasing from the interface G towards the proximal end of the elongated member 201. Also, the shaft 208 may form a stopper, to prevent over penetration of the device.

It should be noted that with the device configuration of FIG. 2, the removal of cut tissue is not only assisted by pressure gradient acting from inner side of the body towards its outer side as will be further described below, but also because of the difference in the cross-sectional dimension of the created channel, i.e. the difference between the circumscribed circles of the prism-like portion at the distal and proximal ends thereof, and accordingly increasing gaps between the elongated member and the tissue surrounding it. Formation of a channel with a variable cross-section, small on the distal (inner) side and bigger on the proximal (outer) side, will have double effect on the tissue ejected, since flow goes both towards the lower pressure and the wider cross-section.

Figure 3A:
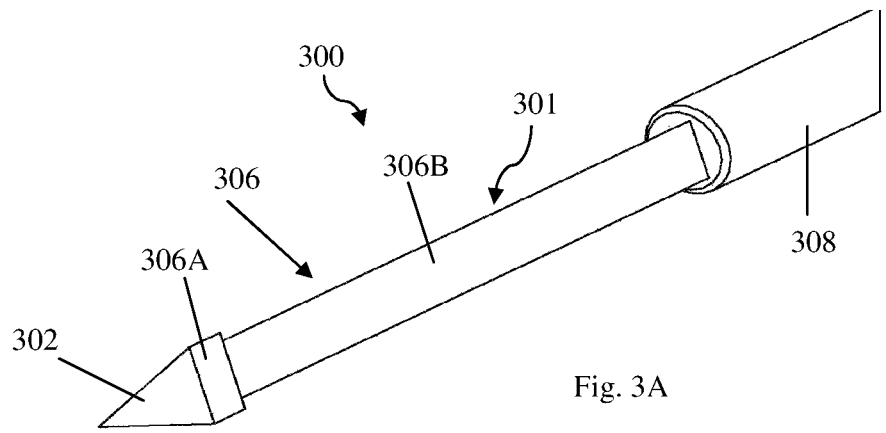
FIGS. 3A and 3B show yet another example of a medical device according to some embodiments of the invention.
Figure 3B:
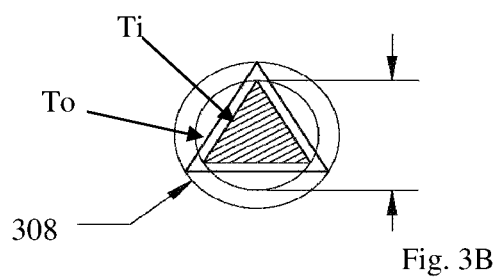

Referring to FIGS. 3A and 3B, a device 300 according to yet another embodiment of the present invention is shown. The device 300 is configured generally similar to the above described device 200, namely includes an elongated member 301 connected to (attached to or integral with) a shaft 308, where the elongated member 301 includes a pyramid-shaped piercing tip 302 directly interfacing at its base with a cutting section/portion 306 and has no penetrating section (104 in FIGS. 1A-1H). The device 300 differs from the above-described device 200 in the configuration of the cutting section 306. The cutting section 306 has two prismatic parts of different cross-sectional dimensions: part 306A adjacent to (interfacing with) the piercing section 302 having a (triangular) cross section To matching that of the pyramid base of the piercing tip, and part 306B with a smaller cross section of a similar polygon (triangle) Ti. The prism section 306A functions as a rake (when the device is pulled back the section 306A sweeps the debris outwards), while the part 306B functions as a cutting element, the cutting blade(s) being incorporated in one or more edges of the prismatic part 306B. FIG. 3B shows how the different cross sections at the different parts of the device relate to each other.

When any of the above-described embodiments of the device of the invention is used to cut tissue, tissue debris is formed by the cutting. While the tissue debris is not harmful to a treated subject, as the biological material is sourced by the subject, it is possible that the debris plugs the tiny tunnel made in the tissue. Thus, it is preferable that the debris be taken outside. Basically, the debris exits the channel by pressure gradients that act on it, because pressure at the distal side, deeper in the tissue, will be higher than pressure at the proximal side, i.e. towards the outside of the tissue/body. This pressure gradient is especially found in a condition such as Glaucoma and assists in the removal of the tissue debris. Insertion of the device into the tissue creates a footprint identical to the shape of the device, e.g. a triangle. When the device rotates, the blade/s path/s open/s a tunnel having open channels (3 such channels in the case of a triangle) in the gap between the tunnel (corresponding to the circumscribed circle of the cutting prism) and the sides/surfaces of the cutting prism. Pressure gradient conveys the debris outside.

Figure 4A:
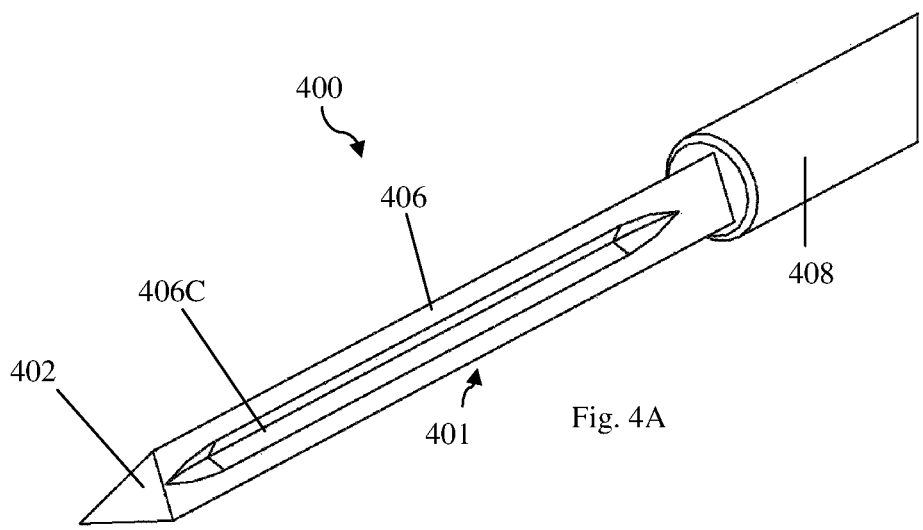
FIGS. 4A and 4B illustrate yet another example of a device according to the invention, where the device includes a cavity in the surface of the prism.
Figure 4B:
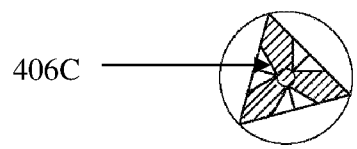

The device of the invention may be further modified to facilitate the removal and collection of the tissue debris. In this connection, reference is made to FIG. 4A-B illustrating a device 400 configured according to an embodiment of the present invention. The device 400 is generally similar to the above-described devices 200 and 300, where the elongated member has no penetration intermediate section, and is more similar to device 200 in that its prism section 406 of the elongated member 401 is a single-part element with the cross section matching that of the base of the pyramid section 402. In the elongated member 401 of device 400, the cutting section 406 is different from that of the device 200 in that each side of the prim 406 is formed with a groove 406C defining a cavity that helps in trapping and collecting the debris during the rotation and cutting process. It should be noted that generally at least one of the prism sides may be formed with one or more grooves. The groove/cavity may be elongated extending along a portion of the surface/side of the prism spaced from its interface with the piercing section, and/or a plurality of spaced-apart grooves/cavities may be formed in a part of at least one surface/side of the prism.

According to the invention, one of the main purposes of including a shaft in the device is to enable reaching deeper tissues by giving more length between the functional cutting part of the device and a driving unit (e.g. a hand-piece machine) that rotates the device mounted to it. In some circumstances, the device has to pass through some tissue before reaching its destination. In this case, when the shaft is at least partly inside the tissue, harm may be done to a tissue that surrounds the rotating shaft. In order to protect the tissue, a protecting sleeve may be positioned around or envelope the rotating shaft, such that the protecting sleeve keeps static and does not rotate with the shaft. Such a sleeve may form part of an engagement protector for engaging the device with a driving unit (rotor machine).

Specifically, if the device is used to create a channel in the sclera tissue of the eye, there is a need to pass through the thin conjunctiva tissue at the front of the eye. If the device has no protecting static sleeve around the shaft, the conjunctiva may wrap around the turning shaft and get torn or harmed and may prevent the device to perform well. Adding a protecting sleeve avoids this harmful scenario while not leaving any foot-print in the conjunctiva tissue after removing the device.

It should be noted that the provision of a protecting sleeve is optional. The device may not use such a sleeve, and in this case the cutting section is rotated in a reciprocating manner (back and forth, e.g. 1-2 turns in each cycle).

Figure 5:
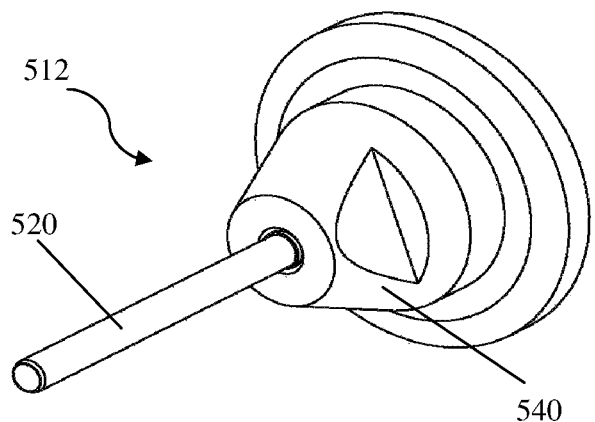
FIG. 5 shows an example of an engagement protector according to an embodiment of the invention.

Reference is made to FIGS. 5 and 6A-D, where FIG. 5 shows an example of an engagement protector 512 according to one embodiment of the invention, and FIGS. 6A-D show different perspective views of the device of the invention engaged with the engagement protector. In this example, the above-described 100 is shown, however it should be understood that any other embodiment of the device according to the invention can be used.

Figures 6A, 6B:
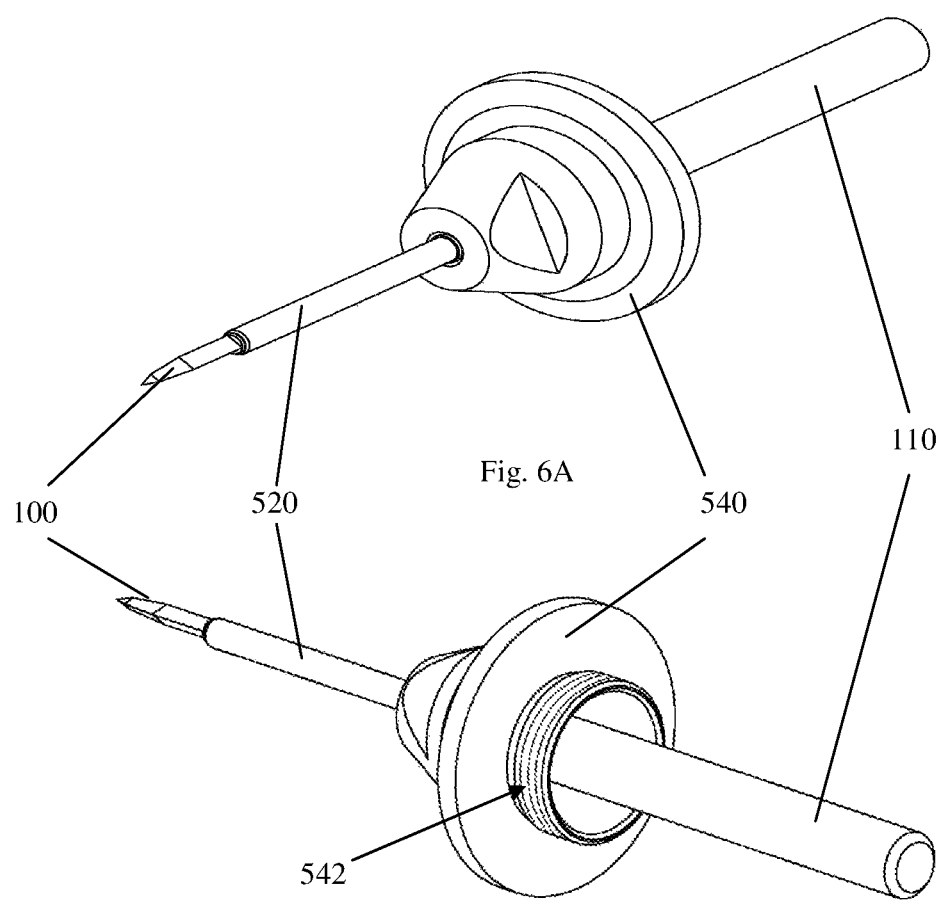
FIGS. 6A-6D exemplify the device of the invention being engaged with the engagement protector.
Figure 6C:
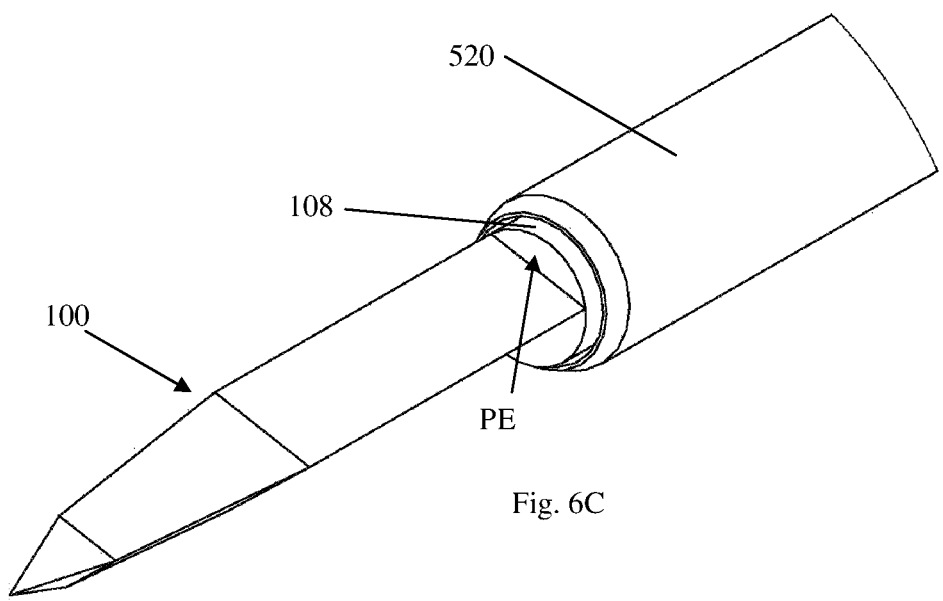
Figure 6D:
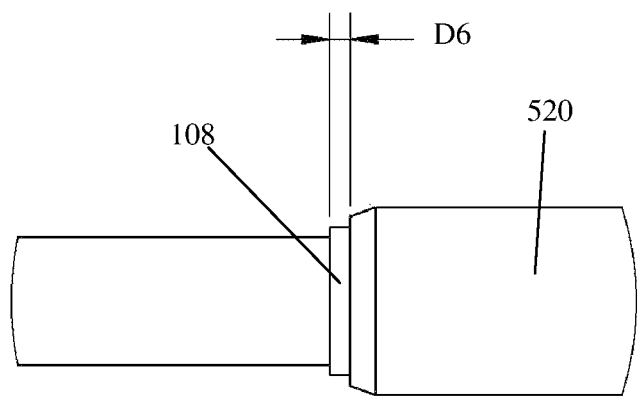

As shown in FIG. 5 the engagement protector 512 includes a protecting sleeve 520 being a hollow cylinder (tube) with an inner diameter configured for inserting at least a portion of the shaft therein. The shaft and the sleeve 520 together are preferably as thin as possible while not compromising robustness and rigidity. As described above with regard to device 100, the interface between the cutting section and the shaft may provide a stopping function. It should be noted that, additionally or alternatively, the protecting sleeve 520 might function by its distal end as a stopper, or might include a stopper (not shown) such as a ridge or a ring at its distal end, to prevent over penetration and/or control the amount of inserting the device into the tissue. The engagement protector 512 includes also an adapter 540 attached to the proximal end of the sleeve 520, the relatively large volume of the adapter 540 facilitates the activity of holding the protector 512 and sliding the device inside the sleeve, gives the protecting sleeve robustness and durability and enables easier attachment to the rotor machine. FIG. 6B shows a thread 542 on the adapter 540, which may be used to attach the protector firmly to the static (e.g.—housing) part of the rotor machine (driving unit). FIGS. 6C and 6D partially show the device 100 and the sleeve 520 in a zoomed perspective. As shown, the sleeve 520 is positioned beyond the shaft 108 with a distance D6 between the distal end of the sleeve 520 and the distal end of the shaft 108. In other words, beyond the stopper PE at the interface between the elongated member and the shaft 108, at which the device stops while being inserted into the tissue. The distance D6 is preferably about 0.1-1 mm along the longitudinal axis of the device. The retracted position of the protecting sleeve 520 is essential in some embodiments, such as when the device is used in creating a channel in the sclera tissue, as in this case it is important for preventing pulling, pinching and tearing the conjunctiva tissue by the rotating device. On the other side, D6 should not be long as in that case the exposed rotating shaft may cause the conjunctiva to wrap around it and get torn or harmed.

As described earlier, the device may be attached to a driving unit (a rotor machine) that rotates it. The driving unit may be configured as a hand-piece machine accepting on it the device as well as the engagement protector. The hand-piece machine may include the rotor inside it, or may serve as a terminal being connected to an external driving unit that includes the rotor, the connection may be wired or wireless. The hand-piece unit may be disposable and configured for one-time use being supplied with the device and engagement protector. The rotor, i.e. the component generating the rotation, which may or may not be included in the disposable hand-piece unit, may be electrically or mechanically driven. One example of such a driving unit/rotor machine and its functionality are described in WO 2013/186779, which is assigned to the assignee of this application and incorporated herein by reference with respect to a specific example. The hand-piece machine is ergonomically constructed to allow ease of access to the treated tissue, thus it may be shaped to fit to the specific surgical site as well as to the operator's comfort. The driving machine may have these parameters adaptable: rotational speed, rotation direction (clockwise, anticlockwise, reciprocating to both side), time of operation, and others. More examples of the build and shape of the hand-piece machine are shown in FIGS. 7A-B and 8A-B.

Figure 7A:
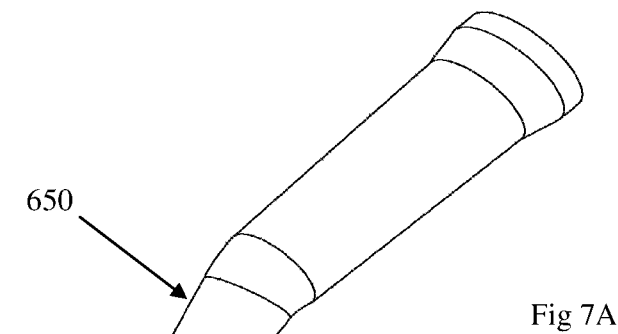
FIGS. 7A and 7B exemplify a device of the invention equipped with a driving unit.
Figure 7B:
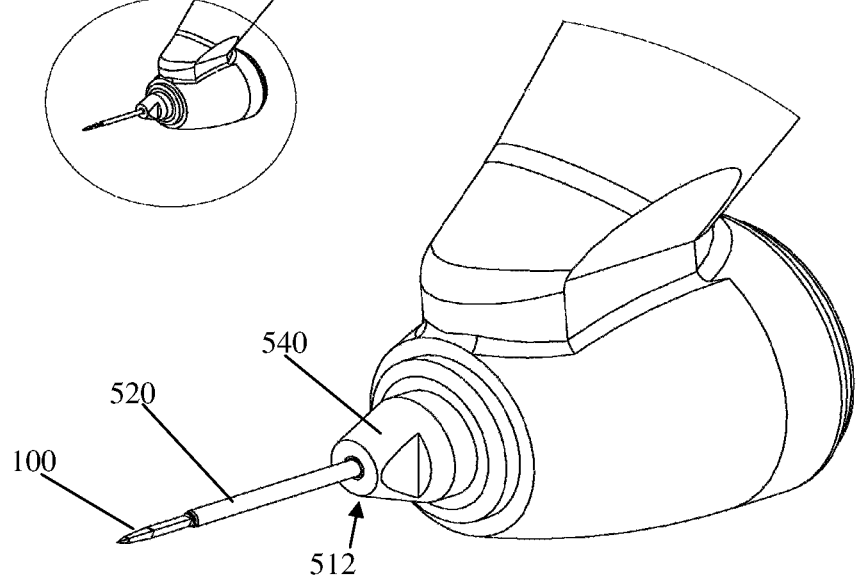

FIGS. 7A and 7B show a hand-piece 650 and the tissue removal device, generally at 100, and the engagement protector 512 having the protecting sleeve 520 and the adapter 540.

Figures 8A, 8B:
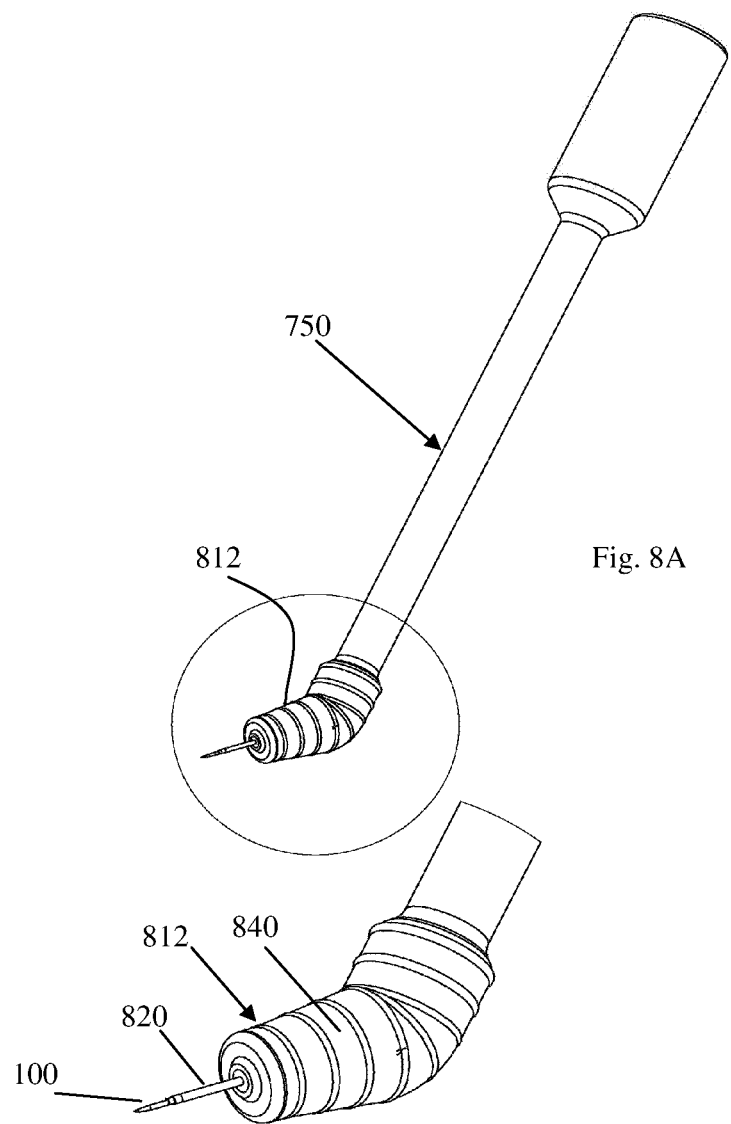
FIGS. 8A and 8B illustrate yet another example of a device of the invention equipped with a driving unit.

FIGS. 8A and 8B show another example of a hand-piece 750 and a device, generally 100, and another example of an engagement protector 812 having a protecting sleeve 820 and an adapter 840.

The invention claimed is:

1. A medical device for removing biological soft tissue by rotating symmetrically with a predetermined high speed around a straight longitudinal axis while inside the soft tissue thereby creating a channel in the biological soft tissue, the device comprising an integral rotatable tool (IRT) extending symmetrically around the straight longitudinal axis, the rotatable tool being formed by a distal elongated member and a proximal shaft, the distal elongated member having a distal end portion and a proximal end portion, said distal end portion being configured as a tissue piercing tip of a pyramid-like shape extending symmetrically around the straight longitudinal axis with proximally increasing cross-sectional area, the medical device being characterized in that said proximal end portion is configured as an elongated prism-like portion extending symmetrically around the straight longitudinal axis and having at least three surfaces and respective prism edges, with at least one of the prism edges between the surfaces being configured as a tissue cutting blade, and said surface and edges having, at each point in the proximal direction, only one of zero and positive slopes, said proximal shaft interfacing with and extending proximally from said proximal end portion and having, at the interface between the proximal shaft and the proximal end portion of the distal elongated member, a cross sectional area larger than a cross sectional area of the proximal end portion of the distal elongated member, and the device being configured at its proximal end for attachment to a rotor machine for rotating the device with the predetermined high speed to create the channel.

2. The device according to claim 1, wherein a base of said elongated prism-like portion at its distal end directly interfaces and matches a base of the pyramid-like shape of the tissue piercing tip.

3. The device according to claim 1, wherein said elongated prism-like portion has a frustum geometry with a proximally increasing cross-sectional area from a distal end towards a proximal end of the elongated prism-like portion.

4. The device according to claim 1, wherein said elongated member comprises an intermediate portion extending between said distal and proximal end portions, said intermediate portion having a frustum shape with proximally increasing cross-section area, a distal base being identical to a base of the pyramid-like shape of the tissue piercing tip and a proximal base being identical to a base of the elongated prism-like portion, thereby forming a smooth transition between the tissue piercing tip and the elongated prism-like portion.

5. The device according to claim 1, wherein said interface between said shaft and said prism-like portion forms a stopper defining the maximal penetration depth of the device into the tissue.

6. The device according to claim 4, wherein the frustum shape of said intermediate portion is defined by a positive slope angle being equal to or smaller than a positive slope angle of the pyramid-like shape of said tissue piercing tip, with respect to the longitudinal axis in the proximal direction.

7. The device according to claim 1, wherein said elongated prism-like portion has a cross sectional area substantially identical to a cross sectional area of the base of the pyramid-like shape of the tissue piercing tip.

8. The device according to claim 1, wherein said elongated prism-like portion has at least a portion thereof of a cross sectional area smaller than a cross sectional area of the base of the pyramid-like shape of the tissue piercing tip.

9. The device according to claim 8, wherein said elongated prism-like portion is formed by successive first and second prismatic portions, the first prismatic portion interfacing with the base of the pyramid-like shape of the tissue piercing tip and having a cross sectional area larger than a cross-sectional area of the second prismatic portion, said at least one tissue cutting blade being constituted by the at least one edge of the second prismatic portion.

10. The device according to claim 9, wherein said first prismatic portion has the cross sectional area matching the cross sectional area of the base of the pyramid-like shape of the tissue piercing tip.

11. The device according to claim 1, wherein at least one of said surfaces of the prism-like portion comprises at least one groove defining a cavity for collecting tissue removed by rotation of the prism-like portion.

12. The device according to claim 1, wherein said prism-like portion, with at least one edge being the tissue cutting blade, is rotatable within its circumscribed circle to thereby cut a ring-like tissue portion in between the circumscribed circle and an inscribed circle of the prism-like portion.

13. The device according to claim 1, comprising a protective sleeve surrounding said shaft along at least a distal part thereof at the proximal end portion of the elongated member, allowing the shaft rotation inside and relative to the protective sleeve.

14. The device according to claim 1, wherein said integral rotatable tool is mounted on an external shank at a proximal end of the shaft, said shank being configured for connecting via its proximal end to the rotor machine.

15. A medical device for removing biological soft tissue by rotating symmetrically with a predetermined high speed around a straight longitudinal axis thereby creating a channel in a biological soft tissue, the device comprising an integral rotatable tool extending symmetrically around the straight longitudinal axis, the rotatable tool being formed by a distal elongated member and a proximal shaft, the distal elongated member being formed by a distal end portion configured as a tissue piercing tip of a pyramid-like shape extending symmetrically around the straight longitudinal axis with proximally increasing cross-sectional area, an intermediate portion, and a proximal end portion comprising one or more tissue cutting elements, the medical device being characterized in that, said intermediate portion extending between the distal end portion and the proximal end portion and having a frustum shape forming a smooth transition between a proximal base of the tissue piercing tip and a distal base of the proximal end portion, the frustum shape having a gradually increasing cross-sectional area towards the proximal end portion and a positive slope angle in the proximal direction, relative to the longitudinal axis, being smaller than a positive slope angle, in the proximal direction, of the tissue piercing tip relative to the longitudinal axis, and said proximal end portion has a zero slope relative to the longitudinal axis, the device having a proximally non-decreasing cross-sectional area from the distal end to the proximal end of the device, and said proximal shaft interfacing with and extending from said proximal end portion and having, at the interface between the proximal shaft and the proximal end portion of the distal elongated member, a cross sectional area larger than a cross sectional area of the proximal end portion of the distal elongated member, and the device being configured at its proximal end for attachment to a rotor machine for rotating the device with the predetermined high speed to create the channel.

16. The device according to claim 15, comprising a penetration stopping element controlling maximal depth penetration of the elongated member into the tissue.

17. The medical device according to claim 15, wherein said proximal end portion comprises an elongated prism-like portion having at least three surfaces and respective prism edges, said one or more of the tissue cutting elements, being constituted by one or more prism edges between the surfaces, being configured as one or more blades.

18. The device according to claim 17, wherein said elongated prism-like portion at its distal end directly interfaces a base portion of the intermediate portion, and said intermediate portion at its distal end directly interfaces a base portion of the tissue piercing tip.

19. The device according to claim 17, wherein at least one of said surfaces comprises at least one groove defining a cavity for collecting tissue removed by rotation of the prism-like portion.

20. The device according to claim 17, wherein said prism-like portion, with at least one edge being the tissue cutting blade, is rotatable within its circumscribed circle to thereby cut a ring-like tissue portion in between the circumscribed circle and an inscribed circle of the prism-like portion.

21. The device according to claim 15, wherein said elongated member, at its proximal end portion, is configured for attaching to an external shank.

22. The device according to claim 18, comprising a protective sleeve surrounding said shaft along at least a distal part thereof at the proximal end portion of the elongated member, allowing the shaft rotation inside and relative to the protective sleeve.

* * * * *